(12) United States Patent
Brandes

(10) Patent No.: US 6,284,799 B1
(45) Date of Patent: *Sep. 4, 2001

(54) CANCER TREATMENT

(75) Inventor: Lorne J. Brandes, Winnipeg (CA)

(73) Assignee: University of Manitoba, Winnipeg (CA)

(*) Notice: Subject to any disclaimer, the term of this patent is extended or adjusted under 35 U.S.C. 154(b) by 0 days.

This patent is subject to a terminal disclaimer.

(21) Appl. No.: 08/773,987

(22) Filed: Dec. 26, 1996

Related U.S. Application Data

(62) Division of application No. 08/505,269, filed on Feb. 23, 1996, now abandoned, which is a continuation of application No. PCT/CA94/00087, filed on Feb. 17, 1994.

(51) Int. Cl.⁷ .................. A61K 31/135; A61K 31/495; A61K 31/50; A61K 31/535

(52) U.S. Cl. .............. 514/651; 514/650; 514/648; 514/252.12; 514/239.2

(58) Field of Search .................. 514/648, 651, 514/650, 239.2, 252.12

(56) References Cited

U.S. PATENT DOCUMENTS 5,618,846 * 4/1997 Brandes .................. 514/641

* cited by examiner

*Primary Examiner*—Jerome D. Goldberg
(74) *Attorney, Agent, or Firm*—Sim & McBurney

(57) ABSTRACT

The present invention is concerned with the identification of compounds which increase the therapeutic index of chemotherapy drugs and which stimulate the growth of cancers, their use in the treatment of cancer and with certain novel compounds useful in such treatment.

8 Claims, 11 Drawing Sheets

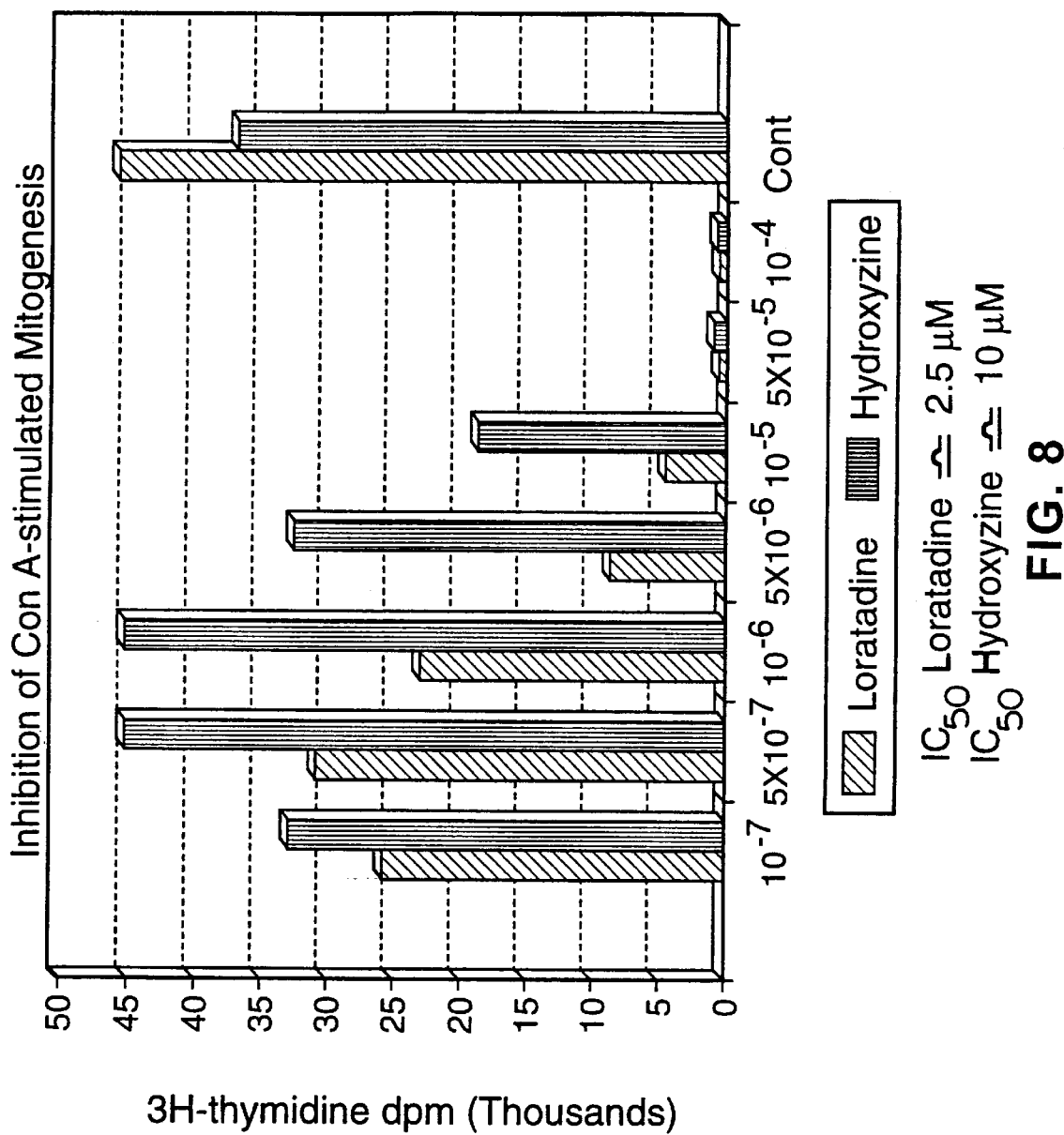

Tumor Growth Promotion (Murine C-3 Fibrosarcoma)
By a Human-Equivalent Daily Dose of Astemizole

CANCER TREATMENT

This is a divisional of application Ser. No. 08/505,269 filed Feb. 23, 1996, now abandoned, which is a continuation of PCT/CA94/00087 filed Feb. 17, 1994.

The present invention is concerned with the identification of compounds which increase the therapeutic index of chemotherapy drugs and which stimulate the growth of cancers, their use in the treatment of cancer and with certain novel compounds useful in such treatment.

BACKGROUND OF THE INVENTION

Over the last 50 years the treatment of a variety of human illnesses has vastly improved with the identification of active drugs and their introduction into clinical use. While perhaps not as dramatic as penicillin or insulin, various clauses of agents, nonetheless, have improved the therapy and/or prognosis of common disorders, including (1) mental illness, especially schizophrenia (e.g. phenothiazines) and major depressive disease (e.g. tricyclic antidepressants and newer, non-tricyclic agents such as fluoxetine); (2) hayfever, asthma, urticaria and other acute allergic disorders (e.g. $H_1$-antagonists); (3) peptic ulcer disease (e.g. $H_2$-antagonists); (4) fungal diseases (imidazoles e.g. clotrimazole, ketoconazole); (5) breast cancer (e.g. tamoxifen); and (6) hypertension, arrythmia and angina (β-adrenergic antagonist). While these seemingly disparate classes of drugs have differing chemical structures, interactions, and indicated uses, in most cases the mechanisms by which they produce their effects are incompletely understood.

For example, although the phenothiazines are known to be antagonists of dopamine ($D_2$) receptors, interactions at many other intracellular sites, including calmodulin, protein kinase C and calcium channels may be important to their activity. Similarly, while antidepressants are known to decrease the uptake of biogenic amine neurotransmitters into nerve endings (especially aerotonin and norepinephrine) thereby increasing their concentration in synapses, a good correlation between potency to inhibit the uptake of any specific amine and potency as antidepressant agents has not been shown.

As another example, while histamine antagonists appear to produce their antiallergic and antiacid effects through binding $H_1$ and $H_2$ receptors, respectively, P450 microsomal enzymes, important in the metabolism of lipids and eicosanoids, have been identified as a major site of binding of the former, as well as of imidazoles. In addition, antidepressant drugs, such as doxepin, do not bind $H_2$ receptors, yet are potent to inhibit acid secretion. As a final example, the antiestrogeni tamoxifen is thought to inhibit breast cancer proliferation through binding estrogen receptors. Yet, it has been reported that tamoxifen is effective in 10% of breast cancers negative for estrogens receptors, suggesting additional mechanisms of action.

Recently, there has been described the existence of unique intracellular histamine receptors, designated $H_{IC}$, in brain membranes and liver microsomes. The paradiphenylmethane derivative, N,N-diethyl-2-[4-(phenylmethyl)-phenoxy]-ethanamine.HCl (DPPE) is a potent antagonist of $H_{IC}$. Surprisingly, the other classes of drugs mentioned above, including phenothiazines, $H_1$ antagonists, serotonin ($5HT_1$, and $5HT_3$) antagonists, triphenylethylene antiestrogens and β-adrenergic antagonists also compete, with varying degrees of affinity, for both DPPE and $H_{IC}$ binding. While $H_2$ antagonists and other imidazoles do not compete for DPPE binding, they do compete for $H_{IC}$, but with lower affinity than for compounds which bind both AEBS and $H_{IC}$.

Through binding $H_{IC}$, histamine functions as Man intracellular messenger to mediate aggregation in blood platelets and is implicated in the proliferation of normal and malignant cells. A second messenger role for histamine at $H_{IC}$ also has been postulated in estrogen action and in brain function. Thus, it is possible that $H_{IC}$ binding may be common to the action of many classes of drugs, including phenothiazines, antidepressants, antiestrogens, histamine ($H_1$, $H_2$, $H_3$) antagonists, serotonin ($5HT_1$, $5HT_3$) antagonists, β-adrenergic antagonists and antifungal agents.

Recently, in published International patent application WO 92/11035, U.S. Ser. No. 711,957 filed Jun. 7, 1991), there is described a novel method of treatment for cancer, combining DPPE or its analogues with chemotherapy drugs, such as doxorubicin (Adriamycin™). In animals and humans, this method of treatment results in the protection of normal stem cells, including bone marrows and mucosal epithelium, while enhancing the anticancer effects of chemotherapy on malignant cells. Although the mechanism of this differential action is not fully understood, in vitro studies indicate that DPPE inhibits normal cell proliferation, in the absence of toxicity, but stimulates malignant cell proliferation and cytotoxicity. Increased response to chemotherapy has been demonstrated in tumor-bearing animals treated concurrently with DPPE. In addition, DPPE also directly cytoprotects normal gut mucosa in vitro, an effect related to DPPE-induced increases in endogenous levels of the protective prggtaglandin, $PGI_2$, and reversed by indomethicin.

SUMMARY OF INVENTION

New data, provided herein, indicate that (1) DPPE alone at low doses directly stimulates tumor cell growth in vivo and (2) increases the inflammatory response in skin elicited by the tumor-promoting phorbol ester, PMA (phorbol myristate acetate). Several other classes of compounds, such as antidepressants, phenothiazines, triphenylethylenes, histamine ($H_1$, $H_2$, $H_3$) antagonists, serotonin ($5HT_1$, $5HT_3$) antagonists, β-adrenergic antagonists and imidazole analogs, also have been identified as producing the same results as those obtained for DPPE.

It now also has been found that tricyclic antidepressant drugs and the non-tricyclic agent, fluoxetine (Prozac™), as well as $H_1$-antihistamines and β-adrenergic antagonists, also compete for the binding of $^3$H-DPPE and $^3$H-histamine to $H_{IC}$ in rat liver microsomes or brain membranes and, likewise, promote tumor growth.

Accordingly, in one aspect of the present invention, there is provided a method for the treatment of cancer cells in an animal, which comprises:

(a) administering to the animal a compound which inhibits normal cell proliferation while promoting malignant cell proliferation in an amount sufficient to inhibit the binding of intracellular histamine in normal cells, and (b) subsequently administering to the animal at least one chemotherapeutic agent for the cancer cells in an amount toxic to the cancer cells. In this way, an enhanced toxic effect on the cancer cells is obtained from the at least one chemotherapeutic agent while adverse side effects of the at least one chemotherapeutic agent on normal cells, including bone marrow and gastro-intestinal cells.

It has been further found that certain fluoro analogs of DPPE exhibit an enhanced potency in inhibiting normal cell proliferation and in promoting malignant cell proliferation and such compounds are novel compounds. Accordingly, in another aspect of the present invention, there is provided a compound having the formula:

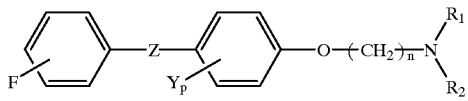

wherein Y is fluorine, chlorine or bromine, Z is an alkylene group of 1 to 3 carbon atoms or a =C=O group, or the phenyl groups are joined to form a tricyclic ring, and p is 0 or 1, $R_1$ and $R_2$ are each alkyl groups containing 1 to 3 carbon atoms or are joined together to form a hetero ring with the nitrogen atom and n is 1, 2 or 3, as well as pharmaceutically-acceptable salts of such compounds.

Such compounds may be prepared by any convenient procedure depending on the identity of the variable groups. For example, for compounds where Z is a carbonyl group, the compound may be made by reacting a hydroxy substituted fluoro-benzophenone with a chloro-substituted amino-substitute alkyl group.

BRIEF DESCRIPTION OF DRAWINGS

FIGS. 1 to 10 are graphical representations of text data generated in certain experiments set forth in the Examples below.

GENERAL DESCRIPTION OF INVENTION

Figure 1:
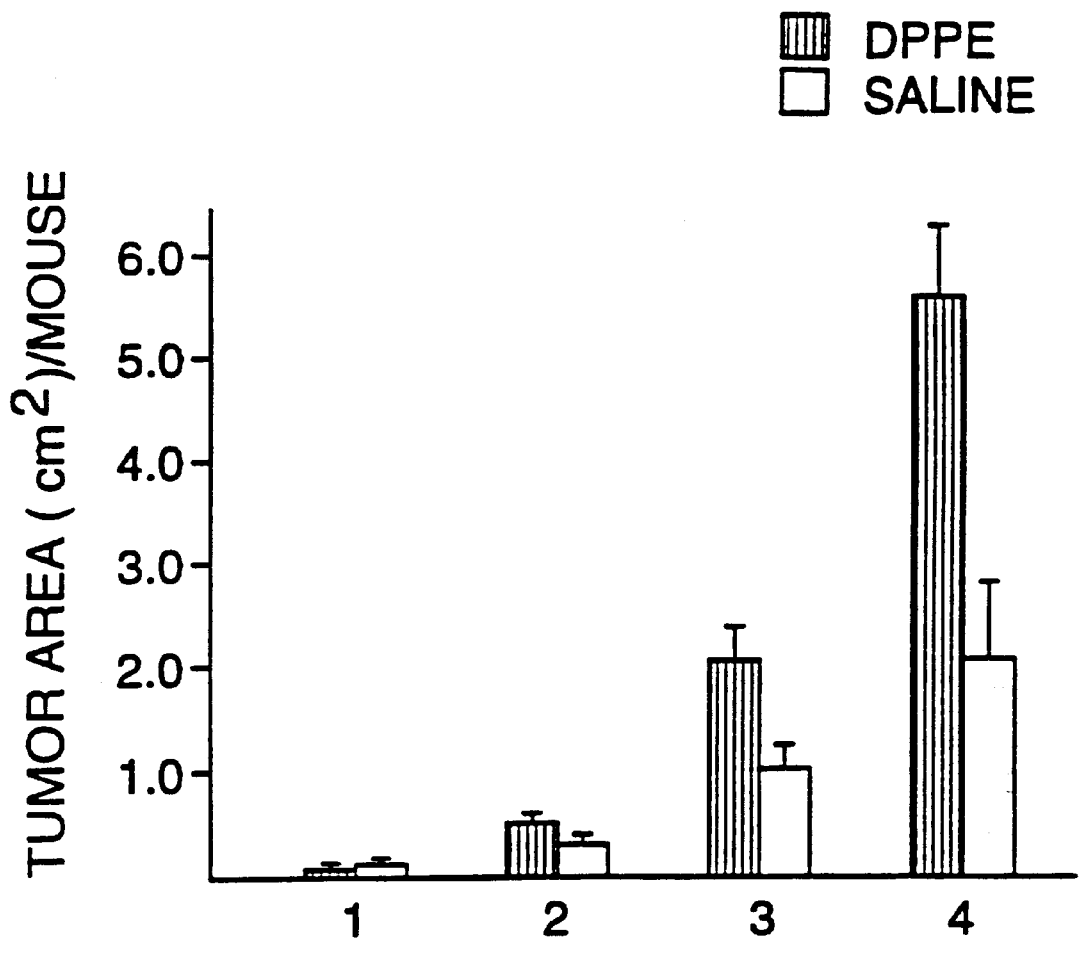

In the present invention, any compound which inhibits normal cell proliferation while promoting malignant cell proliferation is useful and is administered in an amount sufficient to inhibit the binding of intracellular histamine in normal cells. Such compounds generally exhibit a pKi of at least about 5, preferably at least about 5.5.

Specific compounds which are useful in the present invention are diphenyl compounds of the formula:

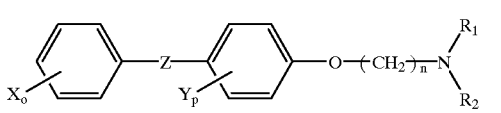

(I)

wherein X and Y are each fluorine, chlorine or bromine, Z is an alkylene group of 1 to 3 carbon atoms or a =C=O group, o and p are 0 or 1, $R_1$ and $R_2$ are each alkyl groups containing 1 to 3 carbon atoms or are joined together to form a hetero-ring with the nitrogen atoms and n is 1, 2 or 3. Pharmaceutically-acceptable salts of the diphenyl compounds may be employed.

Alternatively, the benzene rings may be joined to form a tricyclic ring, in accordance with the structure:

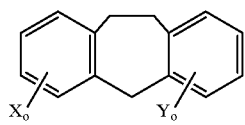

(II)

In one preferred embodiment of the invention, the X group is f, Z is C=O, o is 1, and p is o. More preferably, such compounds have the formula:

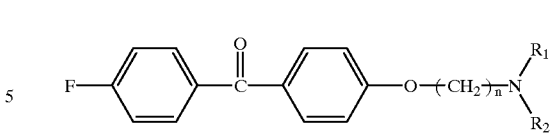

(III)

where n, $R_1$ and $R_2$ are as described above.

In one preferred embodiment, the group

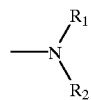

is a diethylamino group, although other alkylamino groups may be employed, such as dimethylamino, and, in another preferred embodiment, a morpholino group, although other heterocyclic ring groups may be employed, such as peperazino. o and p are usually 0 when Z is an alkylene group and n may be 2. In one particularly preferred embodiment of the compounds of formula I, Z is —CH$_2$—, n is 2, o and p are each 0 and

is a diethylamino group. This compound, namely N,N-diethyl-2-[4-(phenylmethyl)-phenoxy] ethanamine, in the form of its hydrochloride salt, is abbreviated herein as DPPE. In addition to a methyl group linking the benzene rings, other linking groups may be employed, such as =C=O. Other substitutions may be made on the benzene rings in addition to the halogen atoms, for example, an imidazole group. In a particularly preferred embodiment, of the compounds of formula III, n is 2 and

is a diethylamino group. This compound, namely N,N=diethyl-2-[4-(4'-fluoro phenone)phenoxy] ethanamine, in the form of its hydrochloride salt, is abbreviated herein as DFPE. This compound exhibits a potency of two to four times that of DPPE in inhibiting normal cell proliferation and promoting malignant cell proliferation in $H_{IC}$ binding competition assays.

Other compounds which may be employed in this procedure include:

(a) tricyclic antidepressants, (e.g. amitriptyline, clomipramine, imipramine and like agents),
(b) non-tricyclic antidepressants (e.g. fluoxetine and like agents),
(c) phenothiazines (e.g. prochlorperazine, trifluoroperizine, chlorpromazine and like agents),
(d) H$_1$-antihistamines, loratadine, hydroxyzine, phenyltoloxamine, astemizole and the like,
(e) β-adrenergic agonists and antagonists (e.g., propanolol and the like),
(f) serotonin (5HT$_1$ or 5HT$_3$) antagonists, such as ondansertron (5HT$_3$) and cyproheptadine (5HT$_1$), (g) imidazoles and imidazole-like compounds, including $H_2$ antagonists, such as cimetidine and ranitidine, $H_3$ antagonists, such as thioperamide and antifungal agents, such as ketoconazole, and (h) triphenylethylene derivatives, such as tamoxifen.

In general, the compounds which may be employed may have a chemical structure consisting of at least two phenyl rings, linked by a rigid third phenyl or non-phenyl ring, or by a non-rigid methyl, oxygen, or other moiety, with the phenyl ring structure being linked by an ether, sulfhydryl or other ring structure or group to a basic alkylamine or imidazole or amino-imidazole side chain, for example, the carboxyamide-amino-imidazole L651582.

Although this wide range of compounds may be employed to increase the therapeutic index of chemotherapy drugs, DPPE and its direct analogs may be a significantly better agent for combination with chemotherapy agents than the foregoing groups of compounds, since DPPE appears to be more potent and selective for $H_{IC}$ and does not interact with calmodulin, protein kinase C, or calcium channels and is only a weak antagonist at other common receptors, such as $H_1$, 5HT and $D_2$.

For example, DPPE does not cause serious toxic effects in humans at clinically relevant doses to enhance chemotherapy (about 0.2–12 mg/kg, preferably less thaws about 10 mg/kg, with about 6 mg being an optimal dose), whereas, for example, at their relevant concentrations to antagonize $H_{IC}$, the antidepressant group of drugs may cause cardiac arrythmias, $H_1$ antagonists might cause marked sedation or even convulsions, and phenothiazines may cause dyskenesias.

EXAMPLES

Example I

This Example illustrates the tumor promoting and proinflammatory response effects of DPPE alone.

FIG. 1 shows the tumor-promoting effect DPPE (1 mg/kg or 4 mg/$M^2$) given subcutaneously once daily×3, to seven DBA/2 mice inoculated subcutaneously with $2×10^2$ L5178Y lymphoma cells 48 hours previously. A second group of 7 tumor cell-inoculated mice served as controls (saline injections, once daily×1). By day 14, 7/7 DPPE treated animals had palpable tumors as compared to 4/7 controls. At the end of 4 weeks, 6/7 controls had tumors with an aggregate surface area of 14.5 $cm^2$ (mean=2.1±0.8 $cm^2$/animal), while 7/7 DPPE-treated animals had tumors with an aggregate surface area of 38.4 $cm^2$ (mean=5.5±0.7 $cm^2$/animal). Thus, the tumor burden of DPPE-treated animals was approximately 2.5-fold greater than that of controls.

To investigate any effect of DPPE to increase PMA-induced inflammation in the same strain of mice (DBA/2), groups of 3 animals were shaved over the back and 48 hours later received a single topical application of 17 nm PMA in acetone. The PMA-treated mice then received either saline (control) or DPPE (4 or 32 mg/kg at time 0 and 24 hours). Three animals painted with acetone served as vehicle controls. Forty-eight hours later, the various groups were sacrificed by $CO_2$ asphyxiation, the skin carefully excised, pinned to paper strips to prevent, wrinkling, and immersed in formaldehyde. H and E-stained sections of skin were assessed for degree of inflammation.

It was observed that the animals who received DPPE had a significantly greater inflammatory response to PMA as compared to saline or acetone controls. The most intense inflammatory response was seen in animals receiving the high dose (32 mg/kg or 128 mg/$M^2$) of DPPE, where increased mitotic activity in the epithelial layer was also noted as compared to the PMA and saline-treated groups. The results of the experiments reported in this Example clearly show that DPPE enhances the inflammatory response of the tumor promoter PMA. Indeed, since tumor promotion requires the presence of inflammatory response, and can be blocked by agents which inhibit inflammation by definition, DPPE functions as a co-promoter with PMA.

Example II

This Example shows the $H_{IC}$ binding and tumor promoting effects of certain compounds and the antiproliferative effect of DPPE and certain compounds.

Figure 2:
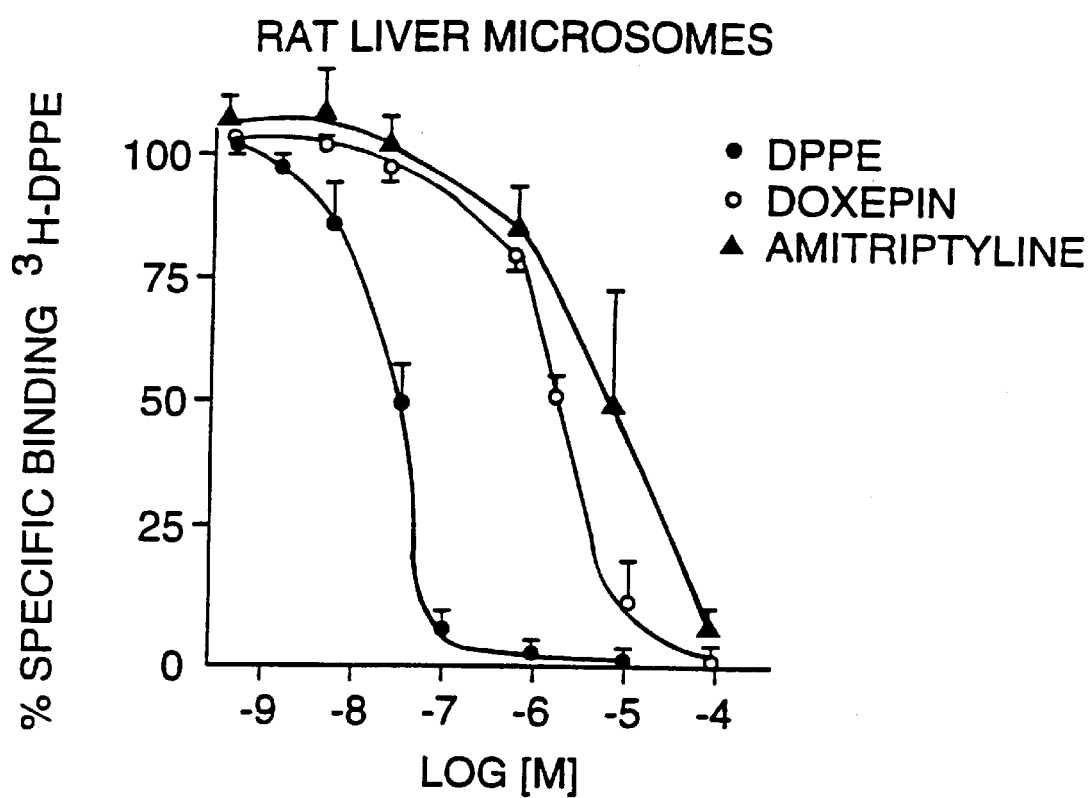
Figure 3:
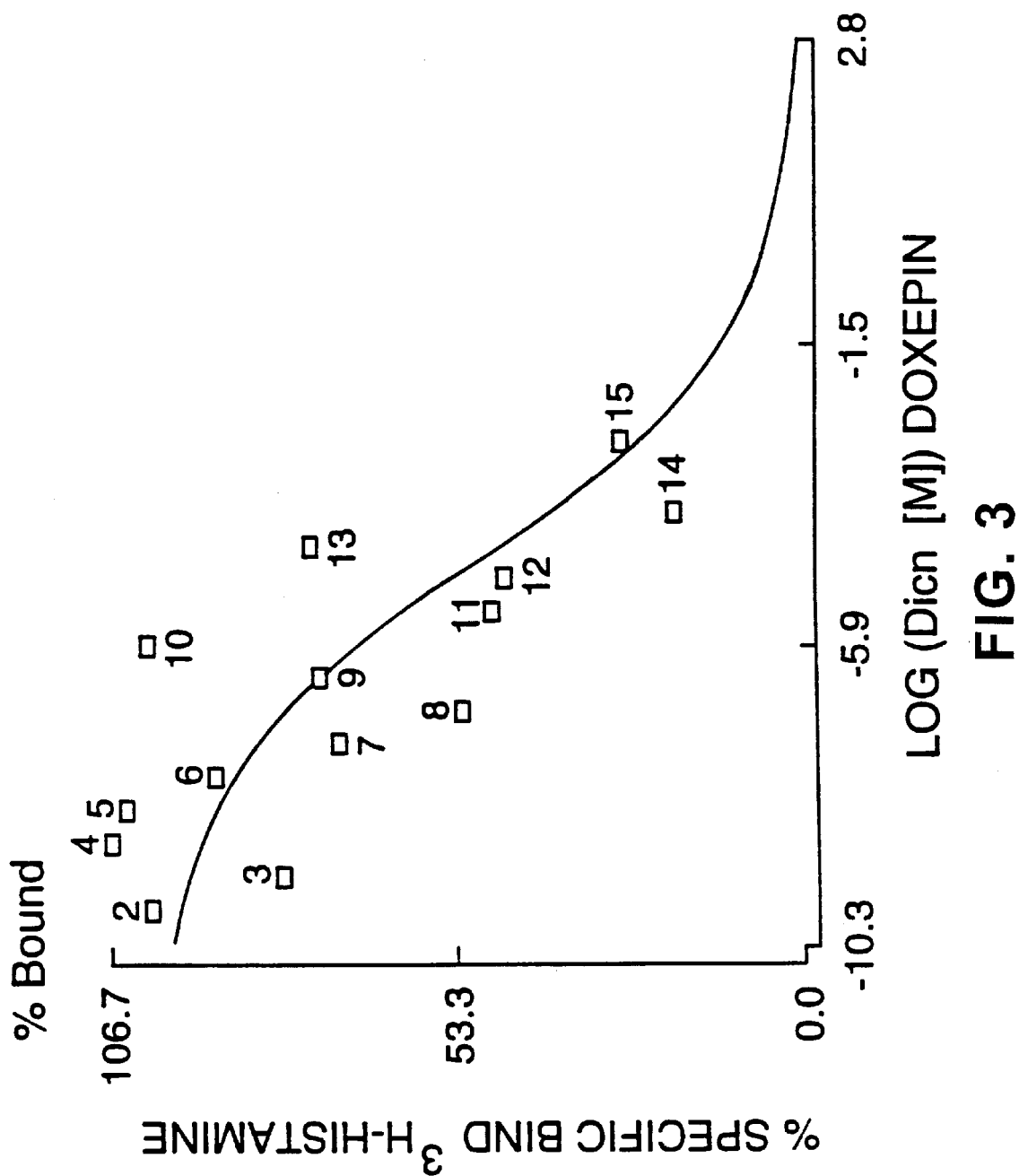

FIG. 2 shows the potency of two tricyclic agents, namely amitriptyline and doxepin, to compete for $^3$H-DPPE binding in liver microsomes. The $K_d$ value for DPPE is 65 nM while the $K_1$ for doxepin is 5 $\mu$M and for amitriptyline is 10 $\mu$M. Doxepin and fluoxetine also compete for $^3$H-histamine binding to $H_{IC}$ in brain membranes ($K_j$=10 $\mu$M; FIG. 3).

Figure 4A:
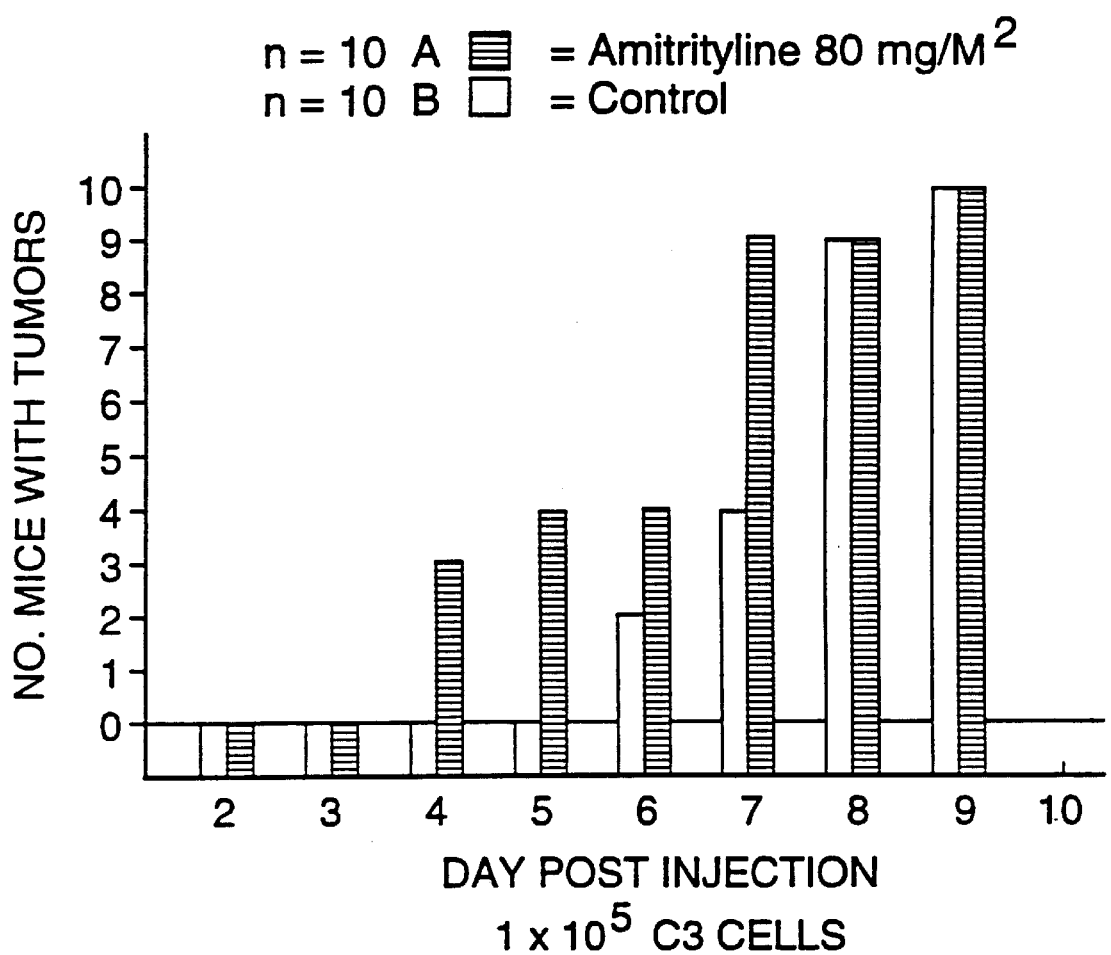
Figure 4B:
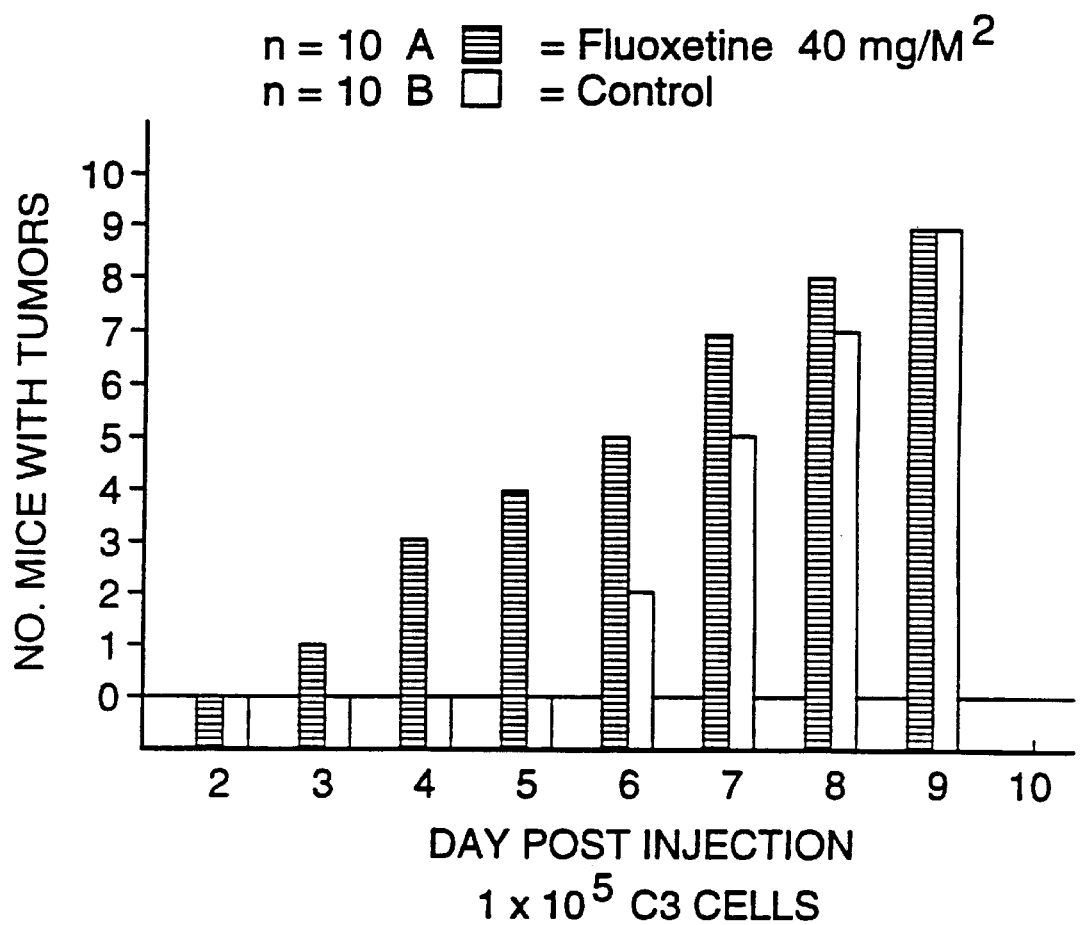

FIG. 4 demonstrates the tumor-promoting effects of the tricyclic agent, amitriptyline, and the non-tricyclic agent, fluoxeting, in C3H mice injected subcutaneously into the gluteal region with $1×10^5$ C-3 fibrosarcoma cells. The doses employed were equivalent to therapeutic human doses (80 mg/$M^2$ for amitriptyline and 20–40 mg/$M^2$ for fluoxetine). The experiments were blinded so that the individual measuring the first appearance of palpable tumor was unaware of the treatment group (saline control vs antidepressant drug; n=10 in each group), It may be seen from this data that, in both experiments, the control animals did not develop tumors until day 6, whereas in the fluoxetine-treated animals, tumors appeared on days 3, 4 and 5 post-injection and, in the amitriptyline-treated animals, tumors appeared on days 4 and 5 post-injection. Thus, in both experiments, 4/10 of antidepressant-treated animals, but no controls had tumors by day 5 (8/20 vs 0/20 controls, both experiments combined).

Figure 5:
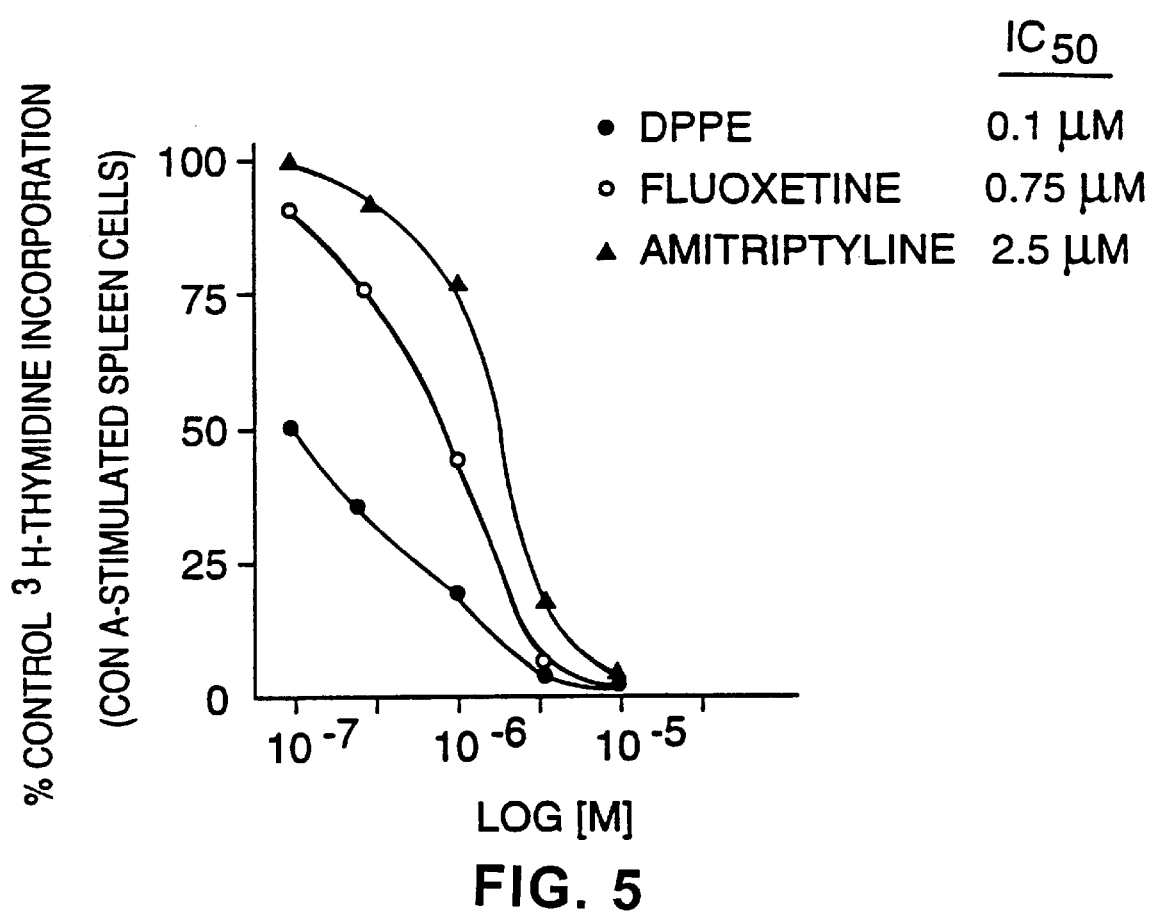

Conversely, FIG. 5 shows that, like DPPE, both amitriptyline and fluoxetine inhibit, in the absence of cytotoxicity, the proliferation of concanavalin A-stimulated normal lymphocytes ($IC_{50=10}$ to 20 $\mu$M). Thus, although weaker than DPPE, these agents inhibit the. proliferation of normal stem cells while increasing the proliferation of tumor cells.

Figure 6:
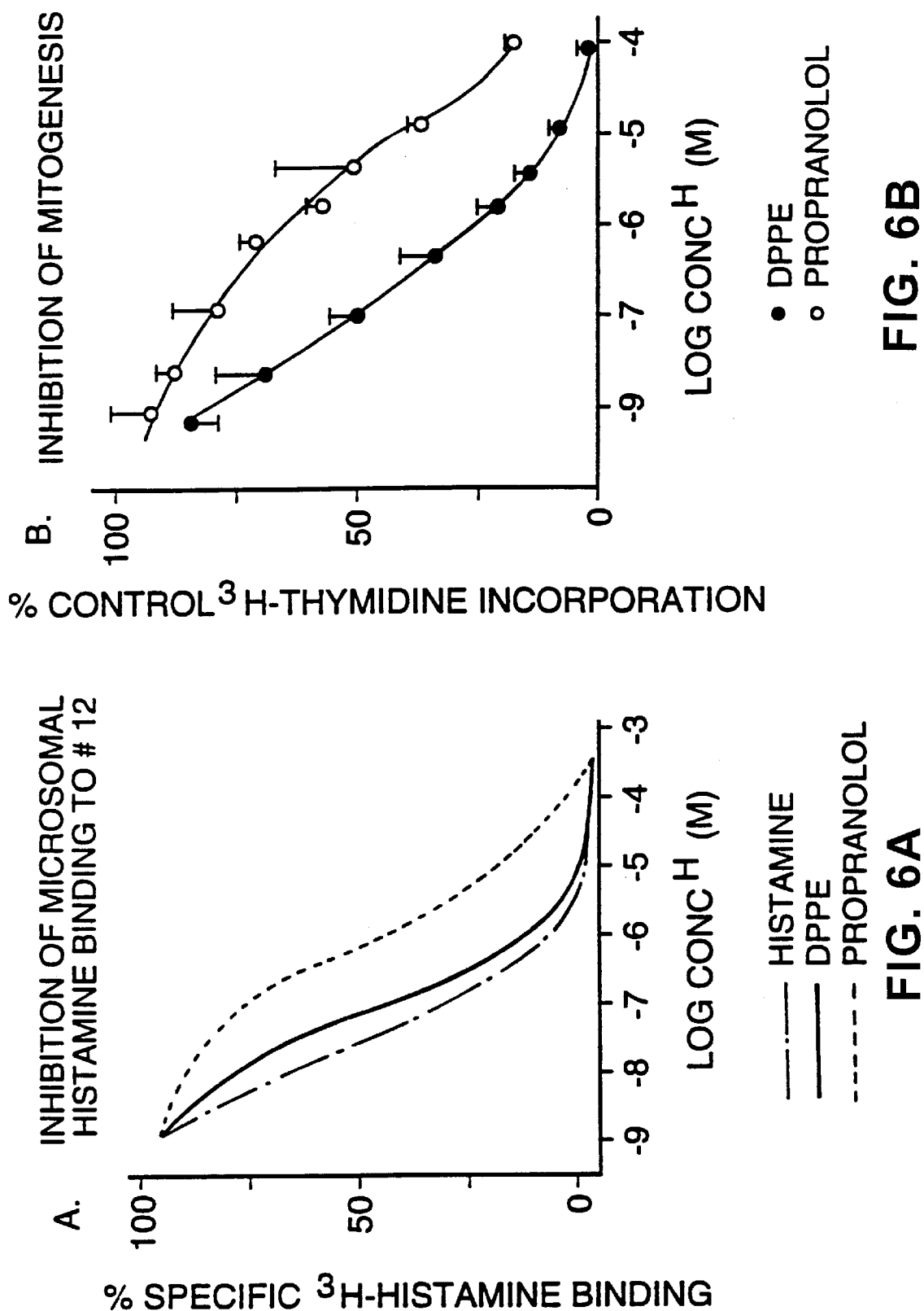
Figure 7:
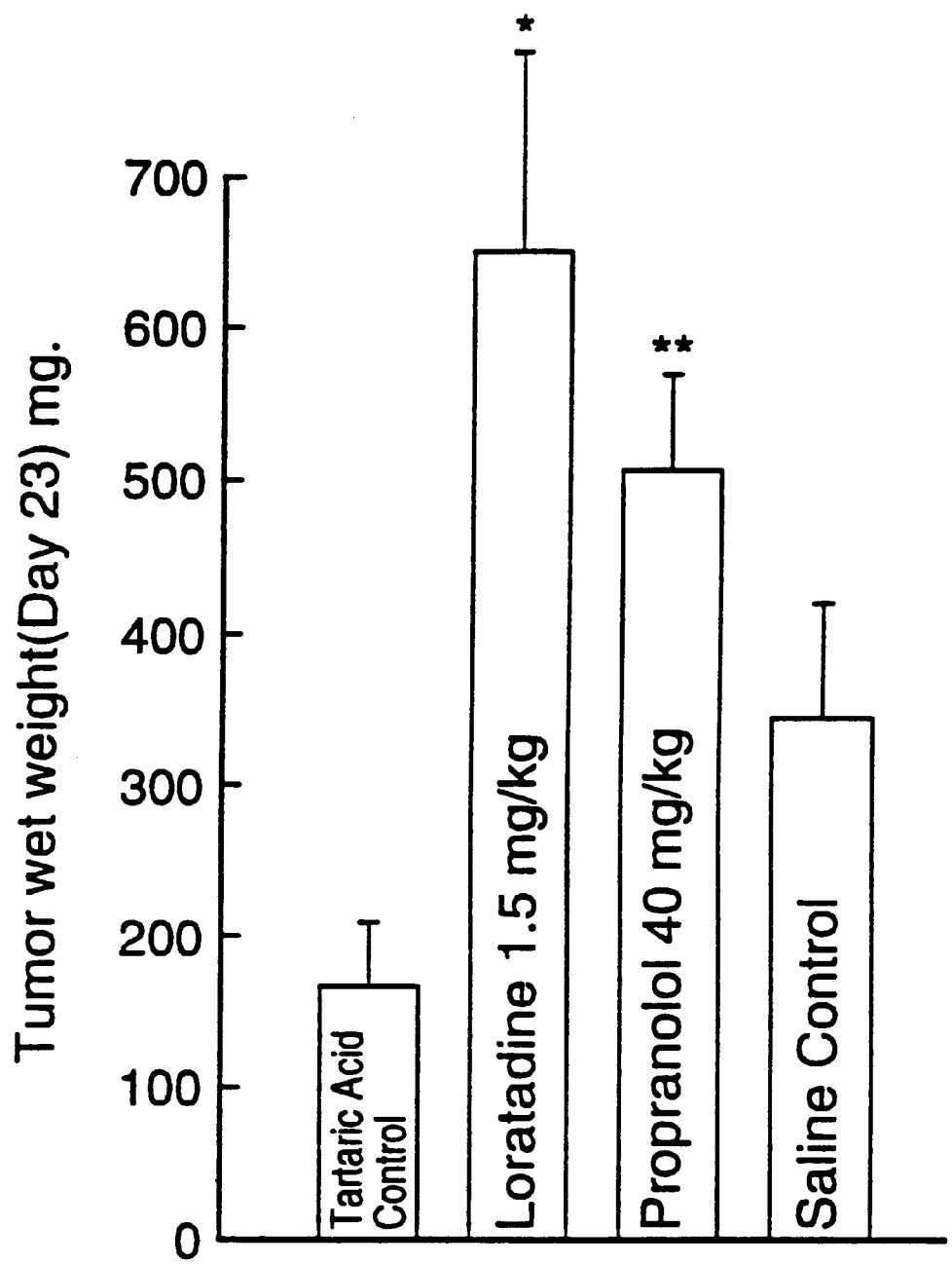
Figure 9A:
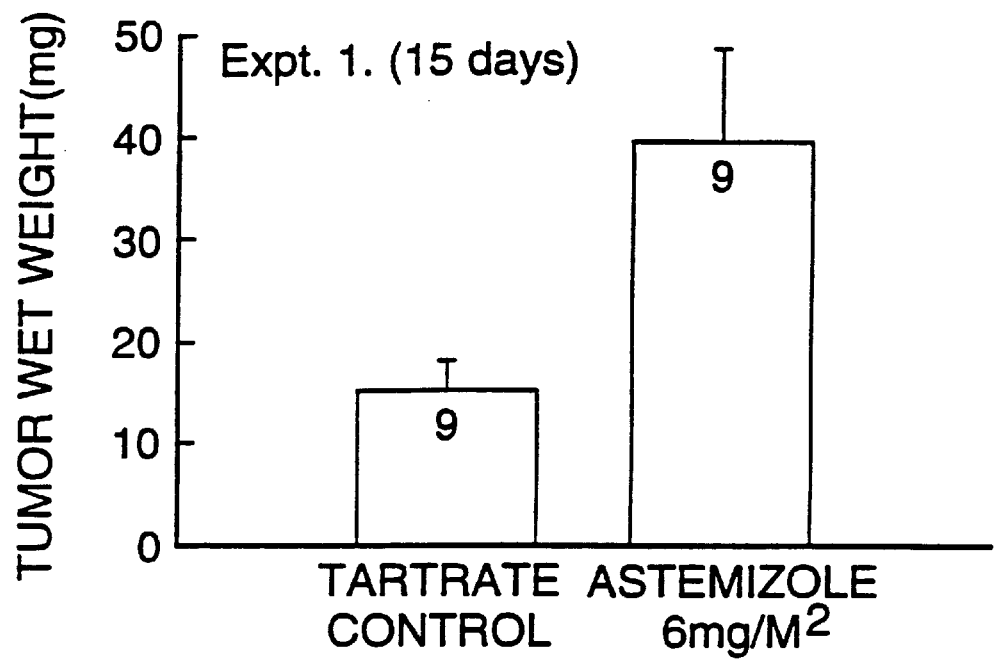
Figure 9B:
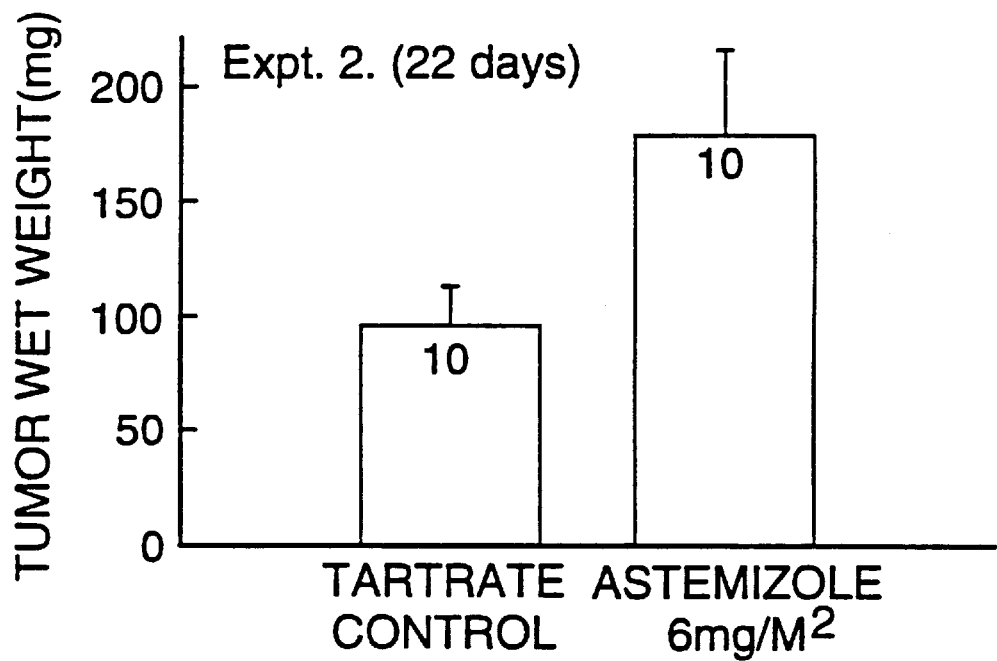

FIG. 6A shows that propanolol (a β-adrenergic antagonist) inhibits histamine binding to $H_{IC}$ in microsomes and FIG. 6B shows that propanolol inhibits normal lymphocyte mitogenesis, In a C-3 fibrosarcoma murine model, propanolol significantly increased tumor weight on Day 23, as seen in FIG. 7. Similarly loratidine (a tricyclic non-sedating $H_1$-antihistamine) potently promoted tumor growth, as seen in FIG. 7, and also inhibited concanavalin A-stimulated mitogenesis (FIG. 8). Astemizole (a non-sedating $H_1$-antihistamine) similarly is potent to inhibit histamine binding and concanavalin A-stimulated mitogenesis (data not shown) and, in two separate experiments, to potently stimulate the growth of C-3 fibrosarcoma, as shown in FIG. 9.

The compounds for which binding and proliferation data are provided in this Example, therefore, mimic the profiles of DPPE to inhibit normal cell proliferation but to promote malignant cell proliferation (Example I). On the basis of his profile, these agents, at the proper dose level, may be predicted to increase the therapeutic index of chemotherapy drugs in the procedure of WO92/11035.

Example III

This Example illustrates the chemical synthesis of N,N-diethyl-2-[4-(4'-fluorophenone)phenoxy] ethanamine.

Diethylaminoethyl chloride.HCl (2 grams) was dissolved in 50 ml H$_2$O made basic with potassium hydroxide, extracted four times with 25 ml toluene to form the base and dried overnight in the presence of Na$_2$SO$_4$. Five grams of 4-fluoro-4'-hydroxy-benzophenone was added to a heated mixture of 50 ml of distilled toluene containing sodium hydride (600 mg). The DEAE base (step 1) was added drop-wise to the benzophenone/toluene and the mixture was refluxed for twenty hours. The mixture was cooled to room temperature and then washed three times with approximately 150 ml of toluene. The toluene wash was taken to dryness. The resulting precipitate was taken up in ethanol and was recrystallized using etheral.HCl. The crystallization was repeated a second time.

Thin layer chromatography of the resulting crystals; showed a single product with a melting point of 128° C., and a molecular weight of 351.5. The IR spectrum of this compound shows a C=O stretch. The structure of DPPE was confirmed by mass spectroscopy and NMR as follows:

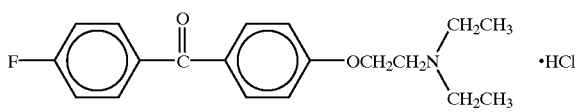

The morpholino-analogue also was prepared using the above-described procedure, but substituting 4-(2-chloroethyl)morpholine.HCl for DEAE.HCl.

Example IV

This Example illustrates the binding characteristics and antiproliferative properties of DPPE.

DFPE competes for [$^3$H] DPPE binding in rat liver microsomes with a K$_I$ value of approximately 70 nM. The K$_i$ value for DFPE approximates the K$_d$ value for DPPE in the same assay. DFPE competes for [$^3$H] histamine binding in rat cortical membranes with a K$_i$ value of 0.3×10$^{-6}$ M. This compares to a K$_i$ value for DPPE in the same assay of 0.9×10$^{-6}$ M; thus DFPE is approximately three times more potent than DPPE in inhibiting histamine binding at a non-H$_1$, non-H$_2$ site (H$_{IC}$) in brain membranes (Brandes, L. J. et al, Cancer Research, 47:4025–4031, 1987).

DFPE antagonizes phorbol myristate acetate (PMA)-induced platelet aggregation with an IC$_{50}$=20 μM; this compares to an IC$_{50}$ value for DPPE in the same assay of 80 μM. Thus, DFPE is approximately four times more potent than DPPE in antagonizing PMA-induced platelet aggregation.

Figure 10:
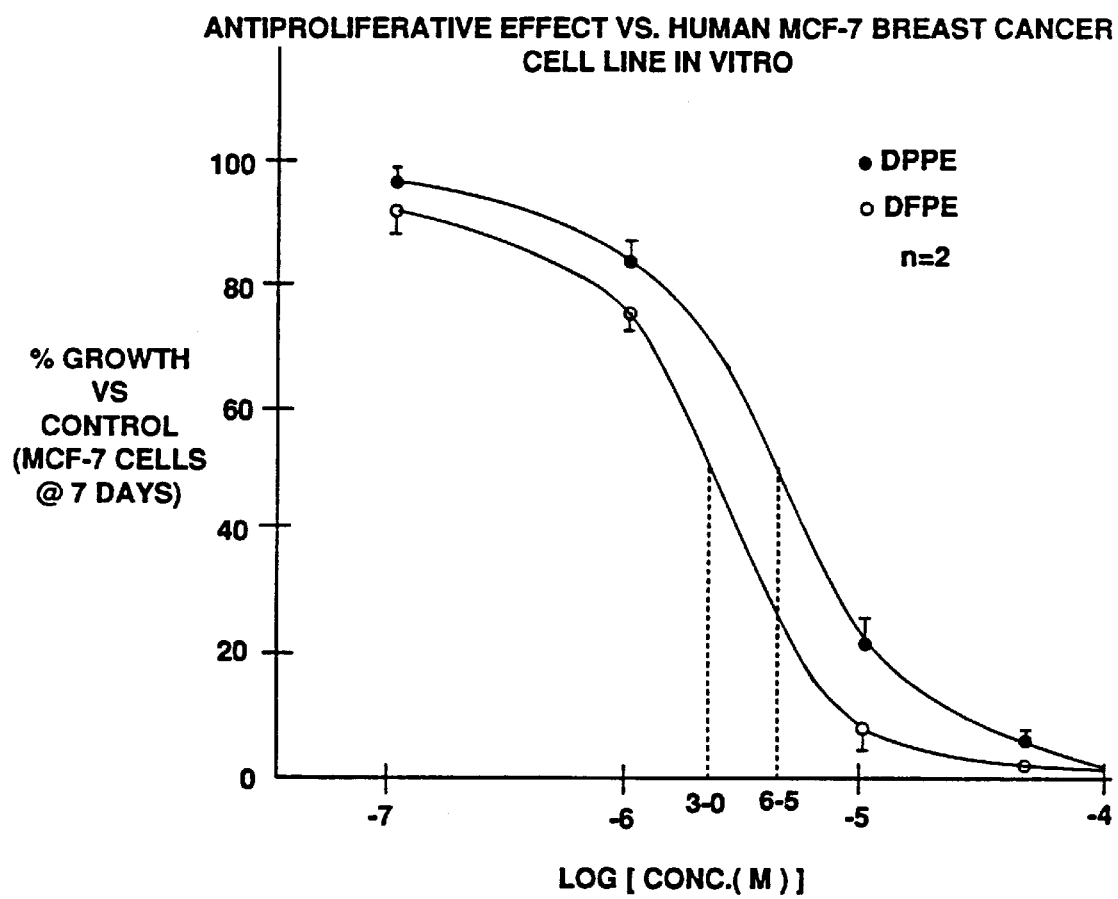

The ability of DFPE and DPPE to inhibit/kill the growth of MCF-7 human breast cancer cells after seven days incubation at 37° C. in vitro is shown in FIG. 10. The IC$_{50}$ value for DFPE is 3.0×10$^{-6}$ M. This compares with an IC$_{50}$ value for DPPE of 6.5×10$^{-6}$ in the same assay.

Thus, DFPE possesses novel antihistaminic properties, antagonizes the effects of phorbol myristate acetate on platelet aggregation, and is antiproliferative cyclotoxic to MCF-7 human breast cancer cells, all with a potency approximately three to four times greater than that of DPPE.

Since DPPE has been demonstrated to be antiestrogenic in vivo, to augment the effects of tamoxifen in the rat uterus in vivo, a similar spectrum of in vivo activity is expected for DFPE, but with an overall potency two to four fold greater than that observed for DPPE. In addition DPPE may be used in place of DPPE in the cancer treatment method described herein to improve the therapeutic index of conventional chemotherapy drugs.

SUMMARY OF DISCLOSURE

In summary of this disclosure, the present invention provides identification of compounds and classes of compounds which stimulate cancer growth and which enable the therapeutic index of chemotherapy agents to be improved. Novel compounds also are described. Modifications are possible within the scope of this invention.

What is claimed is:

1. A method for the treatment of cancer cells sensitive to the combination below in an animal which comprises:

(a) administering to said animal a compound which inhibits normal cell proliferation while promoting malignant cell proliferation and which is a diphenyl compound of the formula:

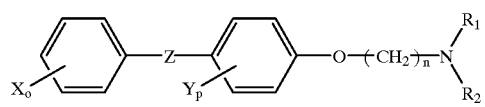

wherein X and Y are each fluorine, chlorine or bromine, Z is an alkylene radical of 1 to 3 carbons or a =C=O group, or the phenyl groups are joined to form a tricyclic ring, o and p are 0 or 1, R$_1$ and R$_2$ are each alkyl groups containing 1 to 3 carbon atoms or are joined together to form a hetero-ring with the nitrogen atom and n is 1, 2 or 3, or a pharmaceutically-acceptable salt thereof, in an effective amount sufficient to inhibit the binding of intracellular histamine in normal cells, and (b) subsequently administering to said animal an effective amount of a chemotherapeutic agent for the cancer cells which is toxic to said cancer cells, whereby an enhanced toxic effect on said cancer cells from said chemotherapeutic agent is obtained while adverse effects of said chemotherapeutic agent on said normal cells is inhibited.

2. The method of claim 1 wherein the group

is a diathylazino group, a dimethylamino group, a morpholino group, or a piperazino group.

3. The method of claim 2 wherein x is a fluoro group.

4. The method of claim 3 wherein said compound is one having the formula:

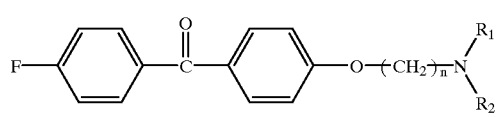

where R$_1$ and R$_2$ are each alkyl groups containing 1 to 3 carbon atoms or are joined together to form a hetero-ring with the nitrogen atom and n is 1, 2 or 3, or a pharmaceutically-acceptable salt thereof.

5. The method of claim 4 wherein the group:

is a diethylamino group, a dimethylamino group, a morpholino group, or a piperazino group.

6. The method of claim 5 wherein

is a diethylamino group, Z is —$CH_2$—, n is 2.

7. The method of claim 6 wherein said compound is in the form of its hydrochloride salt.

8. The method of claim 7 wherein said chemotherapeutic agent is one effective in the treatment of breast cancer.

* * * * *